United States Patent
Rigaut

(10) Patent No.: US 7,658,341 B2
(45) Date of Patent: Feb. 9, 2010

(54) DISPERSION DEVICES FOR AGGREGATES

(75) Inventor: Guillaume Rigaut, Lyons (FR)

(73) Assignee: Merial Limited, Duluth, GA (US)

( * ) Notice: Subject to any disclaimer, the term of this patent is extended or adjusted under 35 U.S.C. 154(b) by 84 days.

(21) Appl. No.: 11/870,059

(22) Filed: Oct. 10, 2007

(65) Prior Publication Data
US 2008/0108137 A1 May 8, 2008

(51) Int. Cl.
*B02B 1/00* (2006.01)
*B02B 5/02* (2006.01)
*B02C 11/08* (2006.01)
*B02C 21/00* (2006.01)
*B07B 4/00* (2006.01)
*B07B 7/00* (2006.01)
*B07B 9/00* (2006.01)
*B07B 11/00* (2006.01)

(52) U.S. Cl. .......................................... 241/39; 241/47
(58) Field of Classification Search ............. 241/38–40, 241/47
See application file for complete search history.

(56) References Cited

U.S. PATENT DOCUMENTS

| | | | |
|---|---|---|---|
| 2,271,982 A | 2/1942 | Van Kreveld | |
| 3,184,168 A | 5/1965 | Feld et al. | |
| 4,919,339 A * | 4/1990 | Niemi | 241/5 |
| 5,143,303 A * | 9/1992 | Niemi | 241/5 |
| 5,598,979 A * | 2/1997 | Rowley, Jr. | 241/5 |
| 6,138,931 A | 10/2000 | Geurts et al. | |
| 6,739,531 B2 | 5/2004 | Taylor | |
| 6,786,437 B2 * | 9/2004 | Ribardi | 241/5 |
| 6,871,806 B2 * | 3/2005 | Tsai et al. | 241/39 |

* cited by examiner

*Primary Examiner*—Bena Miller
(74) *Attorney, Agent, or Firm*—Judy Jarecki-Black; Merial Limited; Thomas Kowalski, Esq.

(57) ABSTRACT

The present invention encompasses a flow-through dispersion device for the dispersion of cell aggregates, the device comprising a first or upstream inlet obstacle and a second or downstream outlet obstacle, each obstacle having at least one traversing hole wherein no two holes align. Between the two obstacles is a turbulence chamber, such that when a cell suspension is passed through the inlet holes, into the chamber and then exits the second obstacle, the turbulence within the chamber disrupts and disperses cell aggregates. The device optionally may have more than two obstacles and turbulence chambers and multiple units may be placed in series to increase the amount of turbulence and time applied to a volume of cells. The invention further encompasses methods of using the device to disperse cell aggregates, and methods of culturing cells that involve seeding cultures and maintaining dispersed individual cells.

12 Claims, 4 Drawing Sheets

DISPERSION DEVICES FOR AGGREGATES

FIELD OF THE INVENTION

The present invention relates to flow-through dispersion devices for dispersion of aggregates, especially of culture suspensions containing cell aggregates. The present invention provides flow-through methods for dispersing aggregates to release individual cells. The present invention further relates to flow-through methods for homogenization of animal cells suspensions containing cell aggregates.

BACKGROUND OF THE INVENTION

During the past 100 years, cell cultures have resulted in many applications in the field of biotechnology. Progress in cell culture, especially in obtaining higher cell productivity, has allowed the development of new processes for production of recombinant proteins and vaccines, biomass and new uses of cells such as cell therapies.

Cells are mainly cultured for two applications. Firstly, cell amplification by subculture will result in increases in biomass production of viable cells. These viable cells can be used for such as cell therapies, for viral infections and to obtain infected cells and the like. The second application is in producing and isolating biological compounds of interest typically, but not always, present inside the cells, such as polynucleotides, proteins, animal pathogens, or fragments thereof. These bioproducts can also be incorporated into other products like DNA vaccines, subunit vaccines, viral vaccines, gene therapy compositions, drugs and the like.

A major problem of the cell culture is the formation of cell aggregates formed during the culture. Cell aggregates, by limiting access of the cells to nutrients and by contact growth inhibition, reduces the culture yield in terms of biomass production and of compounds of interest. In addition, cell aggregation increases cell death, primarily due to apoptosis. For biomass production harvested cells must not be dead or dying to provide for optimal subculturing.

Cells grow either attached to a surface (i.e. anchorage dependent) or in suspension (i.e. anchorage independent). Most cultures of animal cells are anchorage dependent and grow in single-cell layers (monolayers) or on the surface of micro-carriers, in dishes or flasks. Roller bottle technology was developed for cultivating larger number of anchorage-dependent animal cells (Gey G. O., Am. J. Cancer, 17: 752-756 (1933)) although a later improvement came from the use of micro-carriers in bioreactors, which permits an increase in the available growth area for cells per unit of volume (van Wezel A. L., Nature, 216: 64-65 (1967)).

These technologies have now been used for more than 20 years in the pharmaceutical and medical fields for processes such as cell growth and infection, vaccine preparation, recombinant protein expression, and plant cell cultivation. Many of these techniques have been published and are routinely used (See for example Freshney, R. I. Culture of animal cells: a manual of basic techniques: $3^{rd}$ edition 1994).

Typically during culture of anchorage-dependent cells, when the culture reaches confluency, it is desirable to disaggregate the culture into individual cells that retain viability. Cultures of anchorage-independent cells also exhibit cell clusters, and that the problem of cell cluster dispersion exists, irrespective of what type of anchorage the cells have. The resulting disaggregated suspension can then be subcultured or be used directly as a source of a pharmaceutically acceptable compound. Dispersion of cells can be a solution to the inherent problems of cell aggregation but is also problematic, however, due to the fragility of cells resulting in stresses and deaths.

Cells are often so well attached to the underlying culture vessel surface that proteolytic enzymes (such as trypsin, collagenase, pronase), chelating agents (such as ethylenediaminetetraacetic acid) and mechanical forces (such as scraping) (Lloyd et al., J. Cell Sci. 22: 671-684 (1976); Whur et al., J. Cell Sci. 23: 193-209 (1977); Freyer and Sutherland, Cancer Res. 40: 3956-3965 (1980); Lydersen et al., Bio/Technol. 1: 63-67 (1985)). The dispersion of aggregates was also tested with DNAse (Jordan et al. *Animal Cell Technology: Developments, Processes and Products*, eds: Spier et al., 418-420 (1992), pub: Butterworth-Heinemann, Oxford; Renner et al., Biotechnol. Bioeng., 41: 188-193 (1993),) or with hypo-osmolar medium (Leibovitz et al., Int. J. Cell Cloning, 1: 478-485 (1983)). All of these treatments are usually insufficient individually to obtain a uniformly dispersal of viable individual cells. There usually remain some cell clusters visible with the microscope and/or to the naked eye. A cell aggregate or cluster is a mass of variable size, sometimes visible by the naked eye, formed by the union of individual cells together or by the union of cells to at least one other material (i.e. debris, extracellular matrix) present in the initial cell suspension. By definition, a cell aggregate has a minimal size of about 800 μm, in particular a minimal size of about 600 μm, particularly of about 400 μm, preferably of about 200 μm, more preferably of about 100 μm.

Dislodged and dispersed cell suspensions may also need to undergo several downstream treatments, for example to remove chemical compounds used during cell harvest, such as trypsin. These steps are time consuming and increase the cost of the product and may result in undesirable reaggregation. For example, a centrifugation step may be performed to remove undesired chemical compounds. This process, however, leads to the formation of a supernatant containing the chemical compounds and which will be discarded, and a pellet comprising cells to be harvested. When compacted into a pellet, the cells are so close and pushed together that cell aggregates are formed.

Compared to microorganisms such as viruses and bacteria, eukaryotic cells, and especially animal cells, are very fragile and shear sensitive due to the lack of a durable cell wall. Shear sensitivity is also related to the cell type (i.e. whether they are fibroblasts, lung cells, kidney cells, etc.), the culture age and history (old cultures having a high number of passages contain more fragile cells) and maintenance conditions (variations of the culture conditions, such as temperature, osmotic pressure, etc generate stresses). Virus infection may also lead to an increase of the shear sensitivity of infected cells.

In mouse and human cell culture experiments, wall shear stresses of 100 N/m2 over 0.5 seconds residence time cause a significant cell death rate. Studies on embryonic kidney cells showed that shear stresses of less than 0.26 N/m2 caused a slight reduction in viability and no change in cell morphology (Harbour et al., Adv. Biochem. Eng., Vol. 29. pub: Springer-Verlag (New York), (1984)).

As a general consideration, therefore, shear forces applied on a cell suspension could result in a decrease in cell viability. Shearing forces may decrease the yield of the viable cells and can also reduce the ability of the cells to divide by inhibition of cell mitosis.

Since for pharmaceutical use good cell viability is preferred, a gentle method of dispersing a cell suspension containing cell aggregates is needed. The technology used has to be efficient to release individual cells in high production yields, but has also to be gentle enough to avoid significant reduction in viability.

Known cell culture manipulation methods may involve dispersion with gentle methods, for example with gentle pipetting (ECACC Handbook, Fundamental Techniques in Cell Culture. A Laboratory Handbook, "Protocol 5—Subculture of suspension cell lines", 2005, edited by Sigma-Aldrich). Pipetting is typically performed manually by repeated aspiration and rejection of the cell suspension until cell clusters have all disappeared. This manual operation is not, however, consistent and reproducible. Different results can be seen using the same cell culture starting material from one pipette to another, or one operator to another. In addition, shear damage is a function of both shearing time and shearing forces. Pipetting too vigorous and/or over too long a period can damage the cells and result in low viability. Alternatively, pipetting too gently or inconsistently and difficulty of determining when cell clusters have disappeared can result in a poor cell yield because remaining cell aggregates will be discarded during subsequent filtration steps. Beside this lack of robustness, the gentle pipetting technique is tedious and requires open phases that increase the risks of contamination. Pipetting is not amenable to large volume processing.

Accordingly, there is still a need for large-scale processes for the dispersion of cell aggregates, and preferably done in a closed system to avoid contamination risks. The present invention addresses these problems by providing a flow-through dispersion device for dispersion of shear sensitive aggregates, notably culture suspensions containing cell aggregates, while respecting the integrity of the individual cells and flow-through methods for dispersing shear-sensitive cell aggregates to release individual cells.

SUMMARY OF THE INVENTION

The present invention encompasses a flow-through dispersion device for the dispersion of cell aggregates, the device comprising an upstream inlet at one extremity of a conduit, a first or upstream inlet obstacle within the conduit, this upstream inlet obstacle having at least one traversing hole that provides from about 50% to about 99.9% of obstruction of the internal cross-section of the conduit, a second or downstream outlet obstacle inside the conduit, this downstream outlet obstacle having at least one traversing hole providing from about 50% to about 99.9% of obstruction of the internal cross-section of the conduit, wherein the longitudinal axis of any hole through any obstacle does not align with the longitudinal axis of any hole of a preceding or succeeding obstacle, and wherein the distance between two successive obstacles is from about 0.1 to about 10 times the diameter of the smallest hole of either of two successive obstacles, and a downstream outlet at the other extremity of the conduit.

The various embodiments of the device according to the invention encompass, but are not limited to, a first obstacle inside the conduit that may be perpendicular to the direction of the flow circulating through this conduit, this first obstacle having a plurality of holes that may be of any configuration including, but not limited to, circular, ovoid, concentric, rectilinear and parallel to the longitudinal axis of the conduit, and which provide from about 50% to about 99.9% obstruction of the section of the conduit, and at least a second obstacle, also inside the conduit and perpendicular to the direction of the flow circulating through this conduit. This second obstacle may also have a plurality of holes that may be of any configuration including, but not limited to, circular, concentric, rectilinear and parallel to the longitudinal axis of the conduit that create from about 50% to about 99.9% obstruction of the section of the conduit. The holes of the second obstacle are not placed in the same longitudinal alignment as any hole of the first obstacle, and the distance between the first and second obstacles is from about 0.1 to about 10 times the diameter of one hole.

In an advantageous embodiment of the present invention, the device may comprise an upstream inlet at one extremity of a cylindrical-shaped conduit, a first obstacle and a second obstacle inside the conduit and perpendicular to the direction of the flow circulating through this conduit, each obstacle having 3 traversing holes the longitudinal axes of which are parallel to the longitudinal axis of the conduit, and which create about 98% of obstruction of the section of the conduit, the longitudinal axes of the holes of the second obstacle not being in the same longitudinal alignment as the longitudinal axis of any hole of the first obstacle, wherein the distance between the two obstacles is about twice the diameter of the smallest hole of either obstacle, and a downstream outlet at the other extremity of the conduit.

The present invention further provides a flow-through method for dispersion of aggregates, comprising the steps of (1) flowing of a suspension containing cell aggregates through a dispersion device according to the invention, thereby disrupting the aggregates, optionally repeating step (1) by reflowing the suspension through the device or by placing in series more than one of the flow-through dispersion devices according to the invention, and (4) harvesting the suspension containing individual cells.

A further object of the invention is to provide a method of cell culture, comprising the steps of (1) introducing cells to be cultured into a culture batch filled with a culture medium and culturing the cells, (2) flowing the suspension containing cell aggregates obtained in step (1) through at least one flow-through dispersion device according to the invention, thereby disrupting the aggregates, (3) reintroducing the suspension obtained in step (2) and containing individual cells into a cell culture batch, (4) optionally repeating steps (1) to (3), and (5) harvesting the suspension containing individual cells.

These and other embodiments are disclosed or are obvious from and encompassed by, the following Detailed Description.

BRIEF DESCRIPTION OF THE DRAWINGS

The following detailed description, given by way of example, and not intended to limit the invention to specific embodiments described, may be understood in conjunction with the accompanying figures, incorporated herein by reference, in which.

DETAILED DESCRIPTION OF THE INVENTION

Figure 1A:
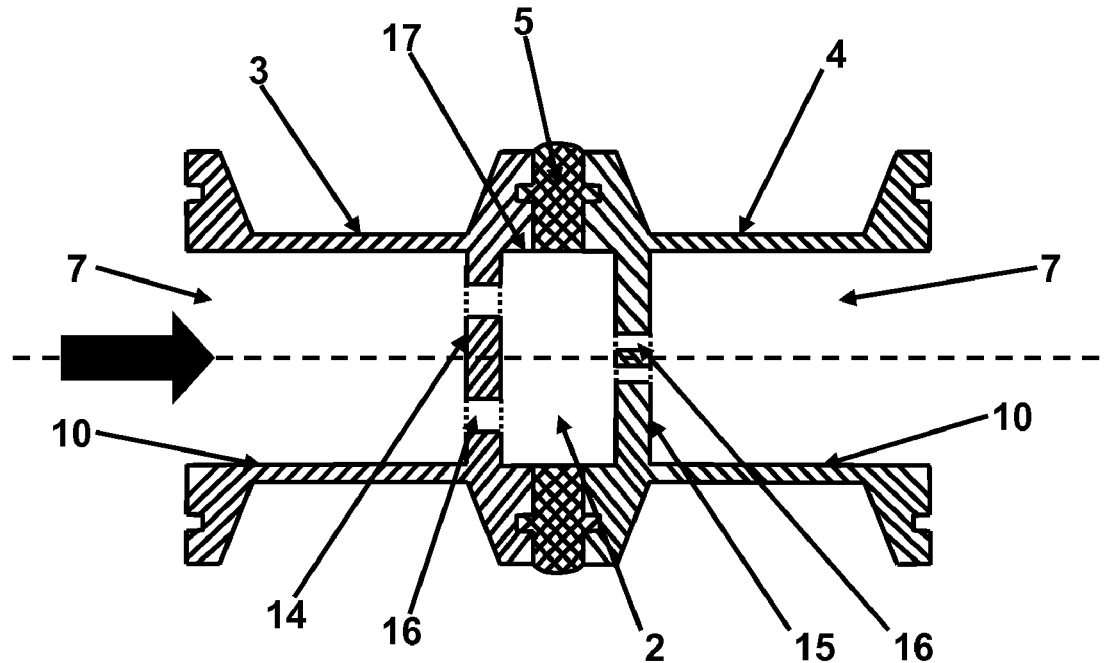
FIG. 1A illustrates a longitudinal section view of a dispersion device comprising two conduit portions connected by a seal, and having single inlet and outlet perforated obstacles and a single turbulence chamber. The direction of fluid flow through the device is indicated by the heavy arrow.

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

The present invention encompasses a flow-through dispersion device for dispersion of aggregates, notably culture suspensions containing cell aggregates. The device, as illustrated for example, in FIGS. 1A-2 and 4A-C, is contemplated to be placed in series with a medium/cell suspension outflow from a cell culture system, whereby the cell suspension may be passed via a conduit (1) of the device and therefore through a turbulence chamber (2). The cell suspension will enter into the flow-through dispersion device via an upstream inlet (3) of the conduit (1) and will exit from the device via a downstream outlet (4) of the conduit (1).

The internal walls (10, 11) of the inlet (3) and outlet (4) of the conduit (1) may have cross section diameters smaller than, equal to or larger than that of the turbulence chamber (2). A cross section of a conduit inlet (3) or outlet (4) is by definition a section perpendicular to the direction of a liquid flow passing through the conduit (1).

There is no restriction as to a particular form of the conduit (1), in particular in the forms of its cross-section. For example the cross-section of the conduit (1) may be, but is not limited to, a circular, ovoid, square or rectangular cross-section. The cross-section of the turbulence chamber (2) is advantageously configured, but not necessarily, to the form of the conduit (1).

The turbulence chamber (2) of the flow-through dispersion device is defined by the opposing internal walls (12, 13) of two obstacles (14, 15 respectively), an upstream inlet obstacle (14) closest to the upstream inlet (3) of the conduit (1), and a downstream outlet obstacle (15) closest to the downstream outlet (4) of the conduit (1), and an inner wall (16) defining the distance separating the obstacles from each other. Each obstacle (14, 15), therefore, is located within the conduit (1) and orientated most advantageously perpendicular to the central axis of the flow-through dispersion device so as to impede the flow of cell culture fluid passing through the conduit (1). It is further contemplated that there may be more than two obstacles as shown, for example, in FIGS. 4A-4C, wherein each adjacent pair of obstacles and the inner wall of the conduit each defines a turbulence chamber (2), thereby forming a plurality of chambers (2) arranged in series. It is further contemplated that the outlet obstacle (15) of a first turbulence chamber (2') may function also as the inlet obstacle for a second turbulence chamber (2") serially located immediately downstream of the first chamber (2') as shown in FIGS. 4A-4C.

Each upstream inlet obstacle (14) and a downstream outlet obstacle (15) is perforated with at least one traversing hole (16) allowing communication of the inlet (3) and outlet (4) of the conduit with the turbulence chamber (2). For the purpose of the flow-through dispersion device of the invention, a traversing hole is defined by an equivalent diameter of a cylindrically-shaped hole having the same section. This equivalent diameter advantageously is at least 25 times greater, more advantageously 50 times greater, and more advantageously at least hundredfold greater than the diameter of an individual live cell of the culture.

The cross-sectional area or combined cross-sectional areas of the traversing hole(s) (16) of an obstacle (14, 15) impedes fluid flow through the conduit (1) from between about 50% to about 99.9%. The fluid flow obstruction, expressed in percentage, is calculated by the following formula $(X-Y)/X$, wherein X is the cross-sectional area of the conduit and Y is the sum of areas of the hole or plurality of holes of the obstacle. Advantageously, the fluid flow obstruction created by an obstacle is from about 50% to about 99.9%. More advantageously, the fluid flow obstruction created by the obstacle may be from about 60% to about 99.9%, more advantageously from about 70% to about 99.9%, more advantageously yet from about 80% to about 99.9%, and most advantageously from about 90% to about 99.9%.

No traversing hole (16) of an upstream inlet obstacle (14) may be concentric with any hole (16) of the immediately succeeding downstream outlet obstacle (15), i.e. the longitudinal axis of one hole (16) is not coincident with the longitudinal axis of any other hole of the flow-through dispersion device as shown, for example, in FIGS. 3A and 3B.

The configurations of the upstream inlet obstacle (14) and downstream outlet obstacles (15) and the traversing holes (16) therein, are not limited as to the thickness of the obstacles which also may be, but not limited to, a circular, ovoid, square or rectangular cross-section, nor in the number, sizes and forms of the traversing holes (16). The traversing holes (16) may also be non-uniform and may have a variety of cross-sections. The device may, for example, have all its obstacles each with one hole. The device may have all its obstacles (14, 15) with several holes (16) having all the same size and form. Alternatively, the device may have obstacles (14, 15) with several holes (16) having different sizes and forms, or each obstacle (14, 15) has the same type of holes but the size and form of holes differ from one obstacle to the other.

It is contemplated that the flow-through dispersion device of the invention may comprise at least two separable portions, an inlet portion (3) and an outlet portion (4) with, as shown for example in FIG. 1A, an optional spacer seal (5) to prevent leakage of fluid from the turbulence chamber (2) and which contributes to the separation between the two opposing obstacles (14, 15). Alternatively, as shown in FIG. 2, the obstacles (14, 15), may be separate and removable from the conduit (1) after separation of the two portions (3, 4). In another embodiment the device is a single integrated unit, as illustrated, for example, in FIG. 4C. It is further contemplated that the flow-through dispersion device may further comprise a securing means (6), as schematically illustrated in FIGS. 1B and 4B for example, for ensuring that the two portions (3, 4) of the device and optionally the spacer seal (5) are operably connected with no leakage of fluids passing through the device. The securing means may be, but is not limited to, a clamp, opposing springs, an elastic seal and the like.

One aspect of the invention, therefore, encompasses a flow-through dispersion device for the dispersion of aggregates, the device comprising an upstream inlet (3) at one extremity of a conduit (1), a first or upstream inlet obstacle (14) within the conduit (1), this upstream inlet obstacle (14) having at least one traversing hole (16) that provides from about 50% to about 99.9% obstruction of the internal cross-section of the conduit (1), a second or downstream outlet obstacle (15) inside the conduit (1), this downstream outlet obstacle (15) having at least one traversing hole (16) providing from about 50% to about 99.9% obstruction of the internal cross-section of the conduit (1), wherein the longitudinal axis of any hole (16) perforating any obstacle (14, 15) does not align with the longitudinal axis of any hole of a preceding or succeeding obstacle, and wherein the distance between two successive obstacles is from about 0.1 to about 10 times the diameter of the smallest hole of either of two successive obstacles, and a downstream outlet (4) at the opposing extremity of the conduit (1).

In various embodiments of the flow-through dispersion device of the invention, the first, or upstream inlet obstacle (14) comprises a plurality of traversing holes (16), wherein the cross-section configurations of the holes (16) may be selected from circular, concentric and rectilinear, and wherein the longitudinal axis of each hole (16) is parallel to the longitudinal axis of the conduit, thereby creating from about 50% to about 99.9% obstruction of the section of the conduit (1), and wherein the holes (16) may be identical or different from one another.

In the embodiments of the flow-through dispersion device of the invention, the second, or downstream outlet obstacle (15) comprises a plurality of traversing holes (16), wherein the cross-section configurations of the holes (16) are selected from circular, concentric and rectilinear, and wherein the longitudinal axis of each hole is parallel to the longitudinal axis of the conduit (1), thereby creating from about 50% to about 99.9% obstruction of the section of the conduit (1), and wherein the holes (16) may be identical or different from one another.

Figure 3A:
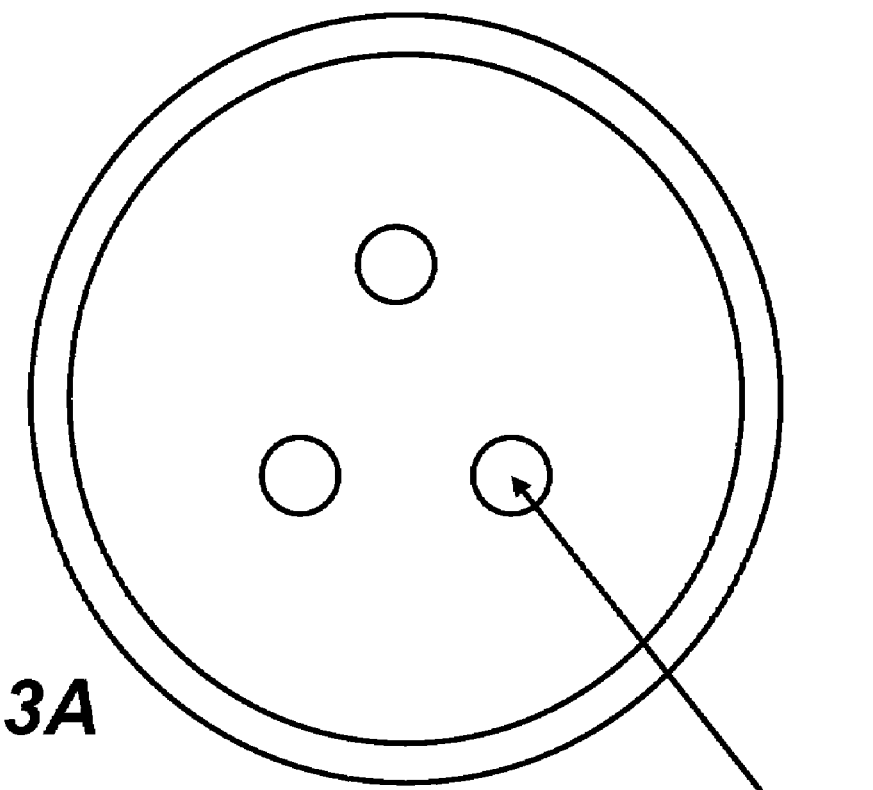
FIG. 3A illustrates a front view of an inlet obstacle.
Figure 3B:
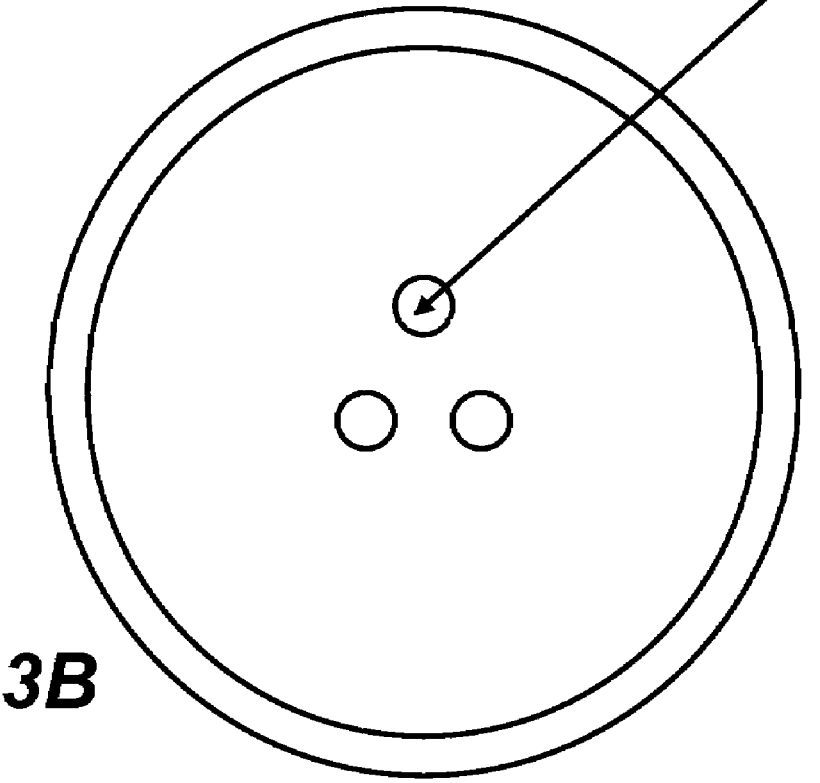
FIG. 3B illustrates a front view of an outlet obstacle, wherein the traversing holes are non-concentric.
Figure 4A:
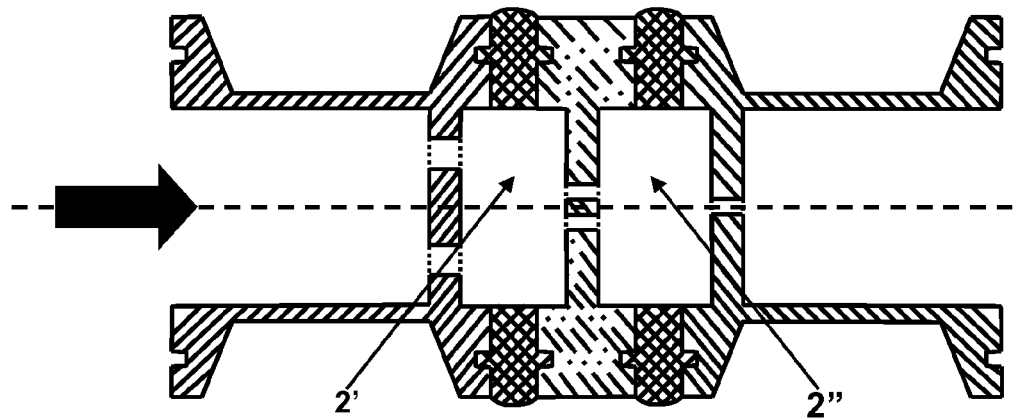
FIG. 4A illustrates a longitudinal section view of an embodiment of the flow-through dispersion device comprising two sequential turbulence chambers.
Figure 4B:
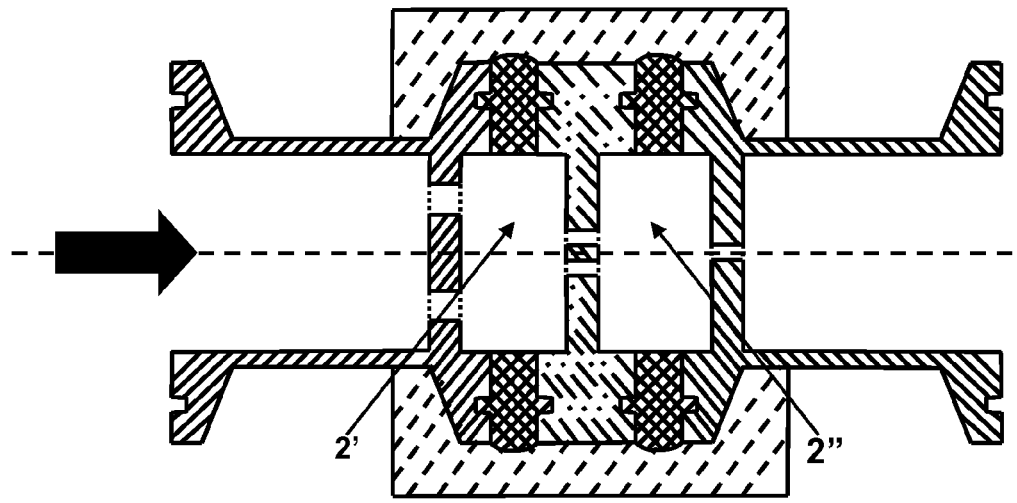
FIG. 4B illustrates a longitudinal section view of an embodiment of the flow-through dispersion device comprising two sequential chambers and a securing means.
Figure 4C:
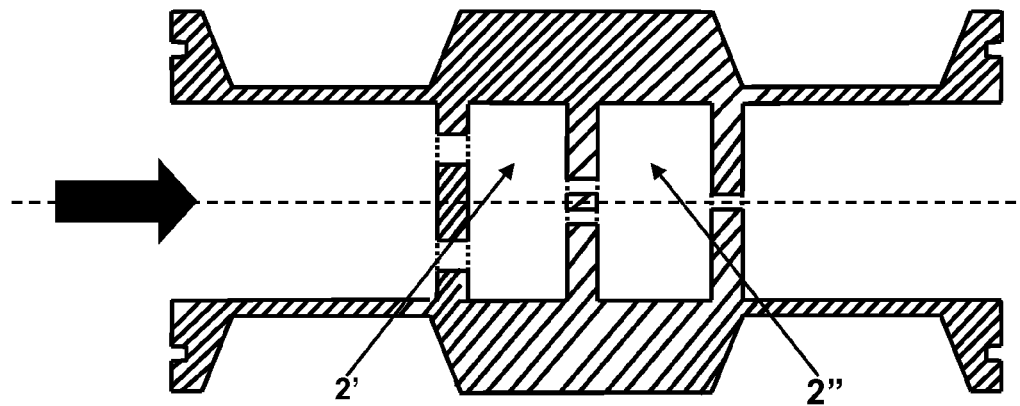
FIG. 4C illustrates a longitudinal section view of an embodiment of the flow-through dispersion device comprising a single unit having two integral turbulence chambers.

In one advantageous embodiment of the flow-through dispersion device of the invention, the first, or upstream inlet obstacle (14), as shown in FIG. 3A comprises three traversing holes (16), wherein the cross-section configurations of the holes (16) may be selected from circular, concentric and rectilinear, and wherein the longitudinal axis of each hole is parallel to the longitudinal axis of the conduit, thereby creating from about 50% to about 99.9% obstruction of the section of the conduit, and wherein the holes (16) may be identical or different from one another, and the second, or downstream outlet obstacle (15) as shown in FIG. 3B comprises a three traversing holes (16), wherein the cross-section configurations of the holes are selected from circular, concentric and rectilinear, and wherein the longitudinal axis of each hole is parallel to the longitudinal axis of the conduit, thereby creating from about 50% to about 99.9% obstruction of the section of the conduit, and wherein the holes may be identical or different from one another and wherein the longitudinal axis of any hole (16) through the first obstacle (14) does not align with the longitudinal axis of any hole of the second obstacle (15).

In the various embodiments of the flow-through dispersion device of the invention, the upstream inlet obstacle (14) and downstream outlet obstacles (15) are advantageously, but not necessarily, perpendicular to the direction of the flow passing through the conduit (1).

In various embodiments of the flow-through dispersion device of the invention, the holes traversing the inlet obstacle (14) and downstream outlet obstacle (15) may be cylindrically-shaped, concentric, or rectilinear, wherein the longitudinal axes of the holes are parallel to the longitudinal axis of the conduit.

Figure 1B:
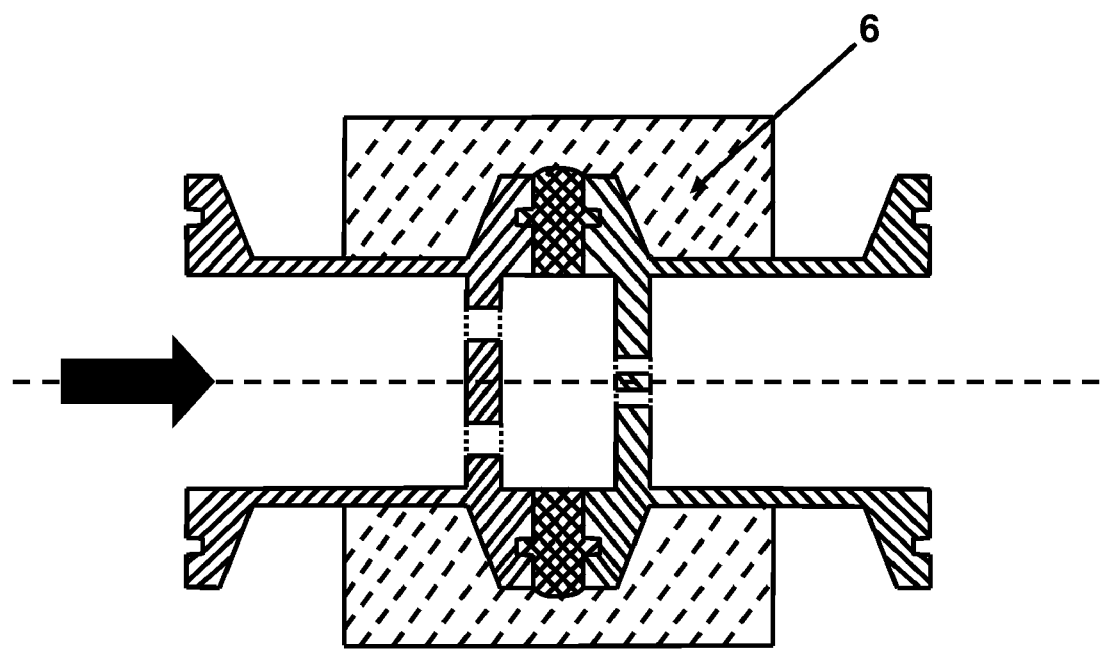
FIG. 1B illustrates a longitudinal section view of a dispersion device comprising two conduit portions connected by a seal and a securing means.
Figure 2:
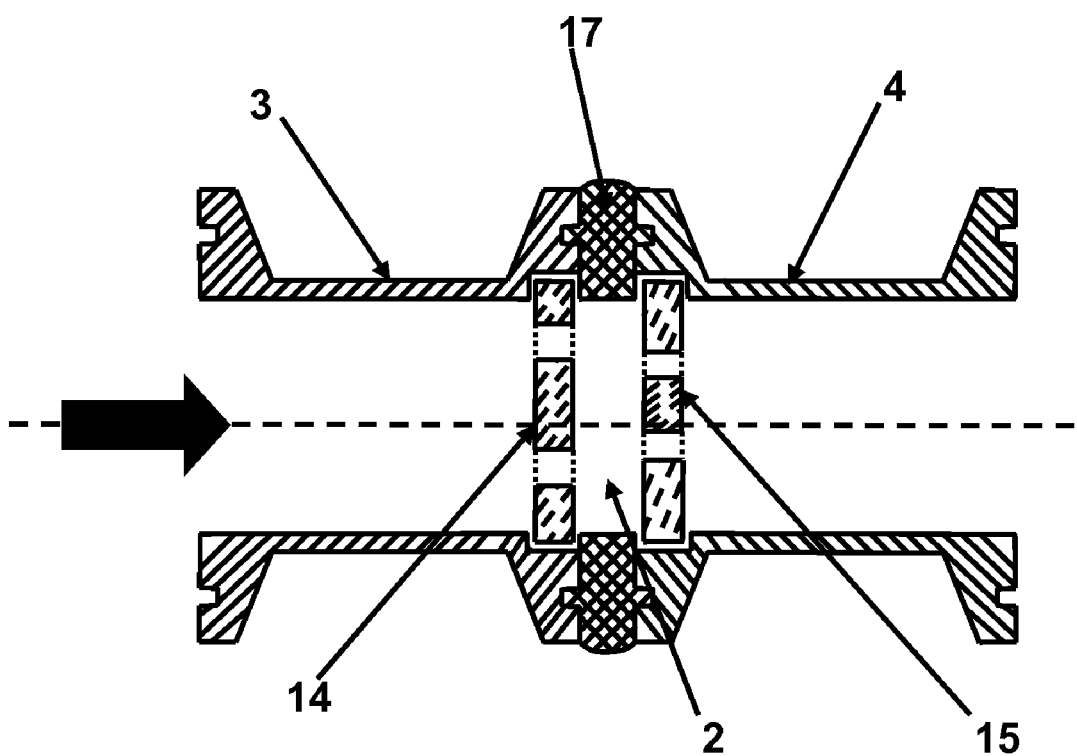
FIG. 2 illustrates a longitudinal section view of a an embodiment of the flow-through dispersion device comprising two conduit portions connected by a seal, and having single inlet and outlet perforated obstacles and a single turbulence chamber, wherein the obstacles are removable plates. The direction of fluid flow through the device is indicated by the heavy arrow.

An advantageous embodiment of the device according to the invention, as shown in longitudinal section in FIG. 1B, comprises a first (3) and a second portion (4), wherein said first (3) and second (4) portions each comprises a conduit (1) having a longitudinal lumen (7) and an obstacle (14,15) located therein and perpendicular to the longitudinal axis of the lumen (7) of the conduit (1) and a spacer seal (5), whereby the first (3) and second (4) portions may be juxtaposed and secured together such that a turbulence chamber is defined by the two obstacles (14, 15), and at least the inner wall (17) of the spacer seal (5). (See Example 1, below, and FIG. 1B).

Another aspect of the present invention encompasses a method of using the flow-through dispersion device according to the present invention. In particular, the present invention encompasses the use of the device according to the present invention to disperse aggregates, especially culture suspensions containing cell aggregates.

In one embodiment of this aspect of the invention, the method for dispersion of aggregates comprises the steps of (1) flowing a suspension containing cell aggregates through at least one flow-through dispersion device according to the invention, (2) disrupting the aggregates, (3) optionally repeating step (1) by repassaging the cell suspension through the device, and (4) harvesting the suspension containing individual cells.

In another embodiment, the method for dispersion of aggregates comprises the steps of (1) flowing of a suspension containing cell aggregates through at least one dispersion device, said device comprising an upstream inlet at one extremity of a cylindrical-shaped conduit; a first obstacle inside the conduit and perpendicular to the direction of the flow circulating through this conduit, this first obstacle having three traversing holes, parallel to the longitudinal axis of the conduit, and wherein the combined cross-sectional area of the holes is about 2% of the total cross-sectional area of the conduit; a second downstream obstacle inside the outlet conduit and perpendicular to the direction of the flow circulating through this conduit, this second obstacle having 3 traversing holes parallel to the longitudinal axis of the conduit, and wherein the combined cross-sectional area of the holes is about 2% of the total cross-sectional area of the conduit, and wherein the holes of the downstream outlet obstacle are positioned relative to the holes of the upstream obstacle so as not to have the same longitudinal alignment that any hole of the upstream obstacle, and wherein the distance between these two obstacles is about twice the diameter of one hole, and a downstream outlet at the other extremity of the conduit, (2) disrupting the aggregates, (3) optionally repeating step (1) by reflowing the suspension through the device(s), (4) harvesting the suspension containing individual cells.

It is also contemplated that in one embodiment of the method of the invention a plurality of the flow-through dispersion devices of the invention may be used for dispersion of aggregates, the devices being placed in serial and the suspension containing cell aggregates flowing through all the devices placed in serial. For example, two to seven devices can be placed in serial or a single device with multiple successive turbulence chambers may be employed.

In another embodiment the dispersion device of the invention is used in a recirculation mode. The cell suspension container is connected to the upstream inlet of the conduit and to the downstream outlet of the conduit. The cell suspension is successively and continuously flowing through the upstream inlet of the conduit, the turbulence chamber, the downstream outlet of the conduit and is recycled inside the cell suspension container. Knowing the processing flow-rate in liters per hour through the dispersion device, the volume of the cell suspension in liter, and the total processing time, it is possible to obtain an average number of passages by multiplying the flow-rate with the total processing time and then divide the resulting value by the volume of cell suspension.

In an advantageous embodiment, three to five dispersion devices may be placed in series, and in a more advantageous embodiment, five dispersion devices are placed serially. Another aspect of the invention is a method of cell culture, comprising the steps of (1) introducing cells to be cultured into a culture medium and culturing the cells, (2) displacing or suspending the cultured cells in a medium, wherein the suspension comprises cell aggregates, (3) passing the cell suspension containing cell aggregates through one flow-through a dispersion device according to the invention or through a serial arrangement of such devices, thereby disrupting the cell aggregates and releasing individual cells therefrom, (4) optionally repeating steps (1) to (3) are repeated as many times as necessary, and (5) reintroducing at least a portion of the disrupted cell suspension from step (3) into the culture batch and reculturing the cells.

In one embodiment of this aspect of the invention, the culture medium may comprise micro-carriers.

In embodiments of this aspect of the invention, it is contemplated that the flow-through dispersion device of the invention may be used in a continuous loop, whereby the culture medium is circulated through the device to disrupt cell clusters as they form.

The devices and methods of the present invention allow in a continuous flow-through mode to subject a cell suspension containing cell aggregates to fluid turbulences to disperse and disrupt the aggregates thereby releasing the individual live cells. The device is a passive device and does not contain any moving part, like rotor or piston, thereby allowing for easy cleaning and reducing the likelihood of damage to the cells.

Turbulence forces are applied to the aggregates during the acceleration of the fluid through the obstacle hole(s) traversing the obstacles and during the reorientation of the flux between two successive obstacles. The distance between two successive obstacles and the fact that the hole(s) of the first obstacle is not placed in the same longitudinal alignment as any hole of the next obstacle creates turbulences. Moreover aggregates, and more specifically macroscopic aggregates, are susceptible to collide with the obstacles, which could also favor aggregate dispersion.

The continuous flow-through mode of the present invention compared to a batch mode (i.e. pipetting method) has the advantage of avoiding dead spaces inside the turbulence system. All the cells pass through the turbulence chamber for an efficient dispersion of aggregates, and consequently the continuous flow-through mode of the present invention results in improved dispersion of the aggregates. The device of the present invention also allows to reduce the open phases by operating in continuous flow-through mode, which results in a decrease of the risk of contamination.

Compared to a rotor/stator agitator and high shear condition, the continuous flow-through mode of the present invention limits the aggregates to a unique and quick passage inside the device. Due to the flow, there is no possibility for the aggregate to pass twice through the holes of the obstacles, and consequently cells are less stressed and the cell viability is better. The processing flow-rate will be adjusted to the device geometry and to the cell type since cell shear sensitivity is related to the cell type, the culture age and history and maintenance conditions. Virus infection usually leads to an increase of the shear sensitivity.

By using an hemocytometer and a microscope, the density of a cell suspension can be easily and quickly established as well as determining the presence or not of cells aggregates. The hemocytometer can also be used to distinguish live cells from dead cells in order to determine the percentage of viable cells. For this purpose it is possible to use vital stain indicators, which stain only nonvital tissues and cells. Cells are permeable to such indicators but live cells are able to exclude them. Dead and dying cells cannot exclude the indicators and therefore display staining. The most commonly vital stain indicator is trypan blue (Hoffmeister E. R., Stain Technol., 28(6): 309-310 (1953); Boedijn K. B., Stain Technol., 31(3): 115-116 (1956); Allison D. C. et al., J. Histochem. Cytochem., 28(7): 700-703 (1980)). By combining such coloration and cell numeration techniques it is possible to readily evaluate the percentage of viable cells in a cell suspension, calculated as the number of living cells/(number of dead cells+number of living cells)×100. It is also possible to obtain the same information by flow cytometry using nucleic acid intercalating agents such as propidium iodide or 7-a aminoactinomycin D (7-AAD) (Wattre P., Ann. Biol. Clin. (Paris), 51(1): 1-6 (1993); Lecoeur H. et al., J. Immunol. Methods, 265(1-2): 81-96 (2002)).

Knowing the percentage of viable cells in a cell suspension, it is easy to determine the optimal conditions that permit obtaining an effective cell dispersion while respecting the viability of the individual cells. One skilled in the art will be able to determine the optimal flow-rate and to determine the optimal number of obstacles in the device or the optimal number of devices to be placed serially to obtain the desired result, i.e. effective dispersion while maintaining the integrity and viability of the individual cells. Ideally, the average velocity of the suspension containing cell aggregates through the holes of the device according to the present invention should be between about 0.1 and about 100 m/s, preferably between about 0.1 and about 20 m/s and more preferably between about 0.5 and about 5 m/s.

Another aspect of the present invention encompasses methods of cell culture, comprising the steps of (1) introducing cells to be cultured into a culture batch filed with a culture medium and culturing the cells, (2) flowing of the suspension obtained in step (1) and containing cell aggregates through at least one device according to the invention and disrupting the aggregates, (3) reintroducing the suspension obtained in step (2) and containing individual cells into the culture batch, (4) optionally repeating steps (1) to (3), and (5) harvesting the suspension containing individual cells obtained after step (2) or step (4).

This can also be done with culture on micro-carriers, i.e. that the culture suspension containing cells/micro-carriers aggregates passes through at least one device according to the invention. During the dispersion of cells/micro-carriers aggregates, the use of the dispersion device according to the invention may allow a reduction in the time needed for dispersion and/or to reduce the added quantity of chelating agents or proteolytic enzymes, notably trypsin. During the chemical or proteolytic dispersion step, the dispersion device according to the invention could be used continuously in recirculation or in a continuous flow-through mode. Another advantage is that the use of the dispersion device according to the invention during the chemical or proteolytic dispersion step results in a better release of the cells from the micro-carriers. This use increases the yield of the cells harvested after the discarding of micro-carriers by clarification.

In another embodiment of the methods according to the invention, at least one dispersion device of the invention can be used continuously in recirculation during cell culture. Depending on the cell type, the culture history and maintenance conditions, cell aggregates can occur during the culture. It would be beneficial to disperse these aggregates into individual cells (i.e. to increase of the contact surface between cells and the culture medium, to avoid apoptosis phenomena). In this particular situation, the dispersion device of the present invention can be used in recirculation because it allows to operate in closed circuit.

The devices and methods of the invention are suitable for use with a variety of cells including, but not limited to, prokaryotic cells such as bacteria and particularly *Escherichia coli* (*E. coli*), and eukaryotic cells such as, but not limited to, yeast, plant cells, and animal cells including insect cells or mammalian cells. The biological compounds of interest are RNAs, DNAs, viruses or phages, proteins. Animal cells particularly suitable for use of the present invention include cells of human, primate, rodent, porcine, bovine, canine, feline, ovine, avian origin and derivatives thereof. In general, animal cells include epithelial cells, which may be primary cells derived from an embryonic tissue sample or adult tissue sample, such as keratinocytes, cervical epithelial cells, bronchial epithelial cells, tracheal epithelial cells, kidney epithelial cells or retinal epithelial cells, or transformed cells or established cell lines (e.g., 293 human embryonic kidney cells, HeLa cervical epithelial cells or derivatives thereof (e.g., HeLaS3), PER-C6 human retinal cells and HCAT human keratinocytes), or derivatives thereof. The cells may be normal cells, or may be genetically altered. Other animal cells, such as CHO cells, COS cells, VERO cells, BHK cells (including BHK-21 cells), CLDK cells, CRFK cells, PK15 cells, MDBK cells, MDCK cells, TCF cells, TDF cells, CEF cells and derivatives thereof, are also suitable for application of the present invention.

The cells are harvested by any means known by the persons skilled in the art, including settling or centrifugation. The cells may be harvested and concentrated by centrifugation, in particular by bucket centrifugation. Further the cells may be stored in a refrigerated form or in a frozen form.

It should be understood that the present invention is not limited to a device or methods described herein and that any device or method steps equivalent to those described falls within the scope of the present invention. It will also be understood that although the form of the invention shown and described herein constitutes advantageous embodiments of the invention, it is not intended to illustrate all possible forms of the invention. The words used are words of description rather than of limitation. Various changes and variations may be made to the present invention without departing from the spirit and scope of the invention.

The invention will now be further described by way of the following non-limiting examples.

EXAMPLE 1

The preparation, propagation and infection of chicken embryo cells with Marek disease virus (MDV) were performed in 1700 $cm^2$ rolling bottles. Infected chicken embryo cells of all the rolling bottles were dissociated by trypsination after attaining 50 to 70% CPE (cytopathic effect), then harvested by centrifugation at 500 g during 12 minutes.

After centrifugation, the supernatant was removed and freezing media was added to the pellet to obtain a cell suspension, but which contained many aggregates clearly visible to the naked eye.

For the dispersion of aggregates, two methods were used. In a first method, the cell suspension from 406 rolling bottles was homogenized by manual pipetting with a 50 ml pipette. The resulting suspension was extemporaneously filtered on a 800 μm Nylon bag, adjusted in volume with some freezing media then analyzed.

In parallel, the cell suspension equivalent of 48 rolling bottles was processed 8 times consecutively through a flow-through dispersion device according to the invention and as illustrated in FIG. 1.

The dispersion device constituted two portions, each one having a conduit (cylindrically-shaped, 34 mm of length and 36.5 mm internal diameter) ending with an obstacle (a plate perpendicular to the conduit axis) (see FIG. 1). Each plate included three cylindrically-shaped rectilinear holes each having a diameter of 3 mm, and equidistant and parallel to the axis of the conduit.

With one portion, the distance between one hole and the conduit axis was 31 mm (see FIG. 2A). With the other portion, this distance was equal to 10 mm (see FIG. 2B model).

The two conduits were joined by opposing the ends of the conduit having the obstacle therein to a distance between the two obstacles of about 6 mm).

The cell suspension recovered after centrifugation was injected through the dispersion device with a flow rate of about 150 l/h by using a peristaltic pump. Samples were taken before and after each passage through the device and analysed after a 800 μm nylon filtration. The injection through the dispersion device and sampling and analysis were reproduced 7 times.

The samples were analysed for quantities of individual cells by visual cell numeration with a Thomas cell, for percentage of viability by FACS (fluorescence activated cell sorting), and for the presence of aggregates by visual observation of the filtration residues. These results are presented in the table 1.

TABLE 1

| Sampling | Individual cell numeration (cells/ml) | Viability (%) | Visual observations | Virus titre (Log10 pfu/ml) |
| --- | --- | --- | --- | --- |
| $1^{st}$ passage Before filtration | 3.0E07 | 80 | Very thick Many large clumps | 6.99 |
| $1^{st}$ passage After filtration | 4.4E07 | 84 | Many clumps Many residues on the filter | 7.05 |
| $2^{nd}$ passage After filtration | 3.8E07 | 77 | Many clumps Many residues on the filter | 7.16 |
| $3^{rd}$ passage | 4.3E07 | 75 | Some clumps | 6.83 |

TABLE 1-continued

| Sampling | Individual cell numeration (cells/ml) | Viability (%) | Visual observations | Virus titre (Log10 pfu/ml) |
|---|---|---|---|---|
| After filtration | | | Less residues on the filter | |
| 4$^{th}$ passage After filtration | 5.2E07 | 71 | Less clumpy few residues on the filter | 7.14 |
| 5$^{th}$ passage After filtration | 5.8E07 | 70 | Very few clumps few residues on the filter | 6.95 |
| 6$^{th}$ passage After filtration | 4.9E07 | 68 | Very few clumps few residues on the filter | 7.17 |
| 7$^{th}$ passage After filtration | 4.8E07 | 66 | Very few clumps few residues on the filter | 7.1 |
| 8$^{th}$ passage Before filtration | 4.4E07 | 68 | Few clumps | 6.9 |
| 8$^{th}$ passage After filtration | 6.2E07 | 69 | Very few clumps few residues on the filter | 6.95 |
| Manual splitting After filtration | 4.1E07 | 63 | Very few clumps Few residues on the filter | 7.02 |

These results show that each passage of the culture suspension containing cell aggregates through the flow-through dispersion device according to the present invention had an effect on the cell aggregates. The viability assessed by FACS analysis decreased with the number of passages, while the number of clumps visible to the naked eye decreased and the viral titre remained stable. With this type of cell culture (with chicken embryo cells infected with MDV) there was an optimum for the use of the device for the dispersion of aggregates with five passages.

These results further show that in-line dispersal of infected cells through a flow-through dispersion device of the invention results in disperse of many aggregates, increased yield of individual cells, and to the retention of more viability compared to when using manual pipetting.

EXAMPLE 2

Preparation, propagation and infection of chicken embryo cells with Marek disease virus (MDV) were performed in 1700 $cm^2$ rolling bottles. Infected chicken embryo cells of all the rolling bottles were dissociated by trypsination after completion of 50 to 70% CPE (cytopathic effect), then harvested by centrifugation at 500 g during 10 minutes. Around 2300 rolling bottles were processed.

After centrifugation, the supernatant was removed and freezing media was added to the centrifugation bucket containing the pellet. The bucket was swirled by hand to obtain a coarse cell suspension, but which still contained many aggregates visible to the naked eye. The cell suspension was stirred during 10 minutes and divided equally into six containers.

One container was processed as a standard without cell splitting. The cell suspension was directly filtered on a cheese-cloth. The filtrate was furthermore diluted with freezing media before filling.

The five remaining containers were split in a continuous way before cheese-cloth filtration and freezing media dilution. For the splitting, the number of dispersion devices (dispersion devices as described in Example 1) and the processing flow-rate were changed from one serial to the other. The final products were analyzed for cell numeration expressed in number of cells per rolling bottles for trial comparison. Results are presented in Table 2.

TABLE 2

| Splitting conditions | Number of roller bottles processed | Individual cell numeration (millions of cells/ rolling bottle) |
|---|---|---|
| Standard | 388 | 423 |
| 3 dispersion devices in series 50 l/h | 388 | 466 |
| 7 dispersion devices in series 50 l/h | 388 | 452 |
| 5 dispersion devices in series 150 l/h | 388 | 466 |
| 3 dispersion devices in series 250 l/h | 367 | 431 |
| 7 dispersion devices in series 250 l/h | 388 | 436 |

These results show that processing of the culture suspension containing cell aggregates through several devices according to the present invention in series had an effect on the amounts of individual cells recovered at the end of the process.

These results show also that the number of flow-through dispersion device elements in series and the processing flow-rate had an impact. Optimal results were obtained for 50 l/h processing flow-rate and 3 dispersion devices in series, and for 150 l/h processing flow-rate and 5 dispersion devices in series.

What is claimed:

1. A flow-through dispersion device for the dispersion of aggregates, the device comprising an upstream inlet at one extremity of a conduit, at least two obstacles having opposing surfaces, said obstacles being a first or upstream inlet obstacle disposed within the conduit, said upstream inlet obstacle being perforated by at least one traversing hole and obstructing from about 50% to about 99.9% of the internal cross-sectional area of the conduit, a second or downstream outlet obstacle disposed within the conduit and a downstream outlet obstacle being perforated by at least one traversing hole and obstructing from about 50% to about 99.9% of the internal cross-sectional area of the conduit, wherein the longitudinal axis of any traversing hole of either obstacle does not align with the longitudinal axis of any other hole of a preceding or succeeding obstacle, a turbulence chamber defined by the opposing surfaces of the first and second obstacles and the inner wall of the conduit between said obstacles, and wherein the distance between two successive obstacles is from about 0.1 to about 10 times the diameter of the smallest hole of either of two successive obstacles, and a downstream outlet at the opposing extremity of the conduit.

2. The device according to claim 1, wherein the inlet to the device conduit and the upstream inlet obstacle form a first portion of the device, and the outlet to the device conduit and the downstream outlet conduit form a second portion of the device and wherein the first and second portions are separable.

3. The device according to claim 2, further comprising a spacer seal.

4. The device according to claim 2, wherein the inlet and outlet obstacles are removable from the device or portions thereof.

5. The device according to claim 1, wherein the upstream inlet obstacle and downstream outlet obstacle are perpendicular to the direction of fluid flow through the conduit.

6. The device according to claim 1, wherein a hole or holes traversing the upstream inlet obstacle and downstream outlet obstacle are parallel to the longitudinal axis of the conduit.

7. The device according to claim 1, further comprising a securing means for maintaining the integrity of the device.

8. The device according to the invention, wherein the inlet conduit, the inlet and outlet obstacles, the turbulence chamber and the outlet conduit are formed as a single integral unit.

9. The device according to claim 1, further comprising at least one additional obstacle thereby defining at least two turbulence chambers.

10. The device according to claim 1, wherein the upstream inlet and the downstream outlet obstacles each comprises three traversing holes, wherein the cross-section configurations of the holes are selected from circular, ovoid, concentric and rectilinear, thereby each creating from about 50% to about 99.9% obstruction of the cross-section of the conduit, and wherein the holes may be identical or different from one another, and wherein the longitudinal axis of any hole through the first obstacle does not align with the longitudinal axis of any hole of the second obstacle.

11. A flow-through dispersion device for the dispersion of aggregates, the device comprising an upstream inlet at one extremity of a conduit, at least two obstacles having opposing surfaces, said obstacles being a first or upstream inlet obstacle within the conduit, the upstream inlet obstacle being perforated by at least one traversing hole and obstructing from about 50% to about 99.9% of the internal cross-sectional area of the conduit, a second or downstream outlet obstacle inside the conduit, and the downstream outlet obstacle being perforated by at least one traversing hole and obstructing from about 50% to about 99.9% of the internal cross-sectional area of the conduit, wherein the upstream inlet obstacle and downstream outlet obstacle are perpendicular to the direction of fluid flow through the conduit and the holes traversing the inlet obstacle and downstream outlet obstacle are parallel to the longitudinal axis of the conduit, and wherein the longitudinal axis of any traversing hole of either obstacle does not align with the longitudinal axis of any other hole of a preceding or succeeding obstacle, and a turbulence chamber defined by the opposing surfaces of the first and second obstacles and the inner wall of the conduit between said obstacles, and wherein the distance between two successive obstacles is from about 0.1 to about 10 times the diameter of the smallest hole of either of two successive obstacles, and a downstream outlet at the opposing extremity of the conduit, wherein the inlet to the device conduit and the upstream inlet obstacle form a first portion of the device, and the outlet to the device conduit and the downstream outlet conduit form a second portion of the device and wherein the first and second portions are separable, and a spacer seal, wherein the turbulence chamber is defined by the opposing surfaces of the two obstacles and the inner wall of the device between the obstacles.

12. The device according to claim 11, wherein the conduit is cylindrical-shaped, the inlet obstacle has 3 holes creating about 98% obstruction of the cross-section of the conduit; the outlet obstacle has 3 holes creating about 98% obstruction of the cross-section of the conduit, wherein the holes of the outlet obstacle do not have the same longitudinal alignment with any hole of the inlet obstacle, and wherein the distance separating these two obstacles is about twice the diameter of any one hole.

* * * * *